(12) United States Patent
Antikainen

(10) Patent No.: US 10,722,208 B2
(45) Date of Patent: Jul. 28, 2020

(54) ALIGNING AN X-RAY MEDICAL IMAGING DEVICE USING THE FRANKFURT PLANE

(71) Applicant: PaloDEx Group OY, Tuusula (FI)

(72) Inventor: Ari Antikainen, Martinkylä (FI)

(73) Assignee: PALODEX GROUP OY, Tuusula (FI)

( * ) Notice: Subject to any disclaimer, the term of this patent is extended or adjusted under 35 U.S.C. 154(b) by 64 days.

(21) Appl. No.: 15/946,310

(22) Filed: Apr. 5, 2018

(65) Prior Publication Data

US 2019/0307415 A1    Oct. 10, 2019

(51) Int. Cl.
| | |
|---|---|
| *A61B 6/03* | (2006.01) |
| *A61B 6/00* | (2006.01) |
| *A61B 6/04* | (2006.01) |
| *A61B 6/06* | (2006.01) |
| *A61B 6/08* | (2006.01) |
| *A61B 6/14* | (2006.01) |

(52) U.S. Cl.
CPC .............. *A61B 6/587* (2013.01); *A61B 6/032* (2013.01); *A61B 6/035* (2013.01); *A61B 6/04* (2013.01); *A61B 6/06* (2013.01); *A61B 6/08* (2013.01); *A61B 6/4007* (2013.01); *A61B 6/14* (2013.01); *A61B 6/4441* (2013.01); *A61B 6/4452* (2013.01); *A61B 6/4458* (2013.01); *A61B 6/501* (2013.01)

(58) Field of Classification Search
CPC ............ A61B 6/587; A61B 6/035; A61B 6/04
See application file for complete search history.

(56) References Cited

U.S. PATENT DOCUMENTS

| | | | |
|---|---|---|---|
| 9,060,716 B2 | 6/2015 | Bianconi et al. | |
| 9,888,891 B2 | 2/2018 | Suuronen et al. | |
| 2007/0183567 A1* | 8/2007 | Rotondo | A61B 6/08 378/38 |
| 2015/0004558 A1 | 1/2015 | Inglese et al. | |
| 2015/0374320 A1 | 12/2015 | Suuronen et al. | |
| 2017/0311915 A1 | 11/2017 | Martino et al. | |

FOREIGN PATENT DOCUMENTS

| | | |
|---|---|---|
| EP | 2959835 A1 | 12/2015 |
| WO | 2016/087894 A1 | 6/2016 |

OTHER PUBLICATIONS

International Search Report and Written Opinion for Application No. PCT/EP2019/057661 dated May 17, 2019 (13 pages).

* cited by examiner

*Primary Examiner* — Hugh Maupin

(74) *Attorney, Agent, or Firm* — Michael Best & Friedrich LLP

(57) ABSTRACT

Aligning an X-ray source in an X-ray imaging system. The system includes a column, an upper shelf coupled to the column through a pivoting joint, a rotating part rotatably coupled to the upper shelf, the rotating part comprising a first X-ray source, a laser, and an X-ray imaging detector. The system also includes a patient support attached to the column with a first arm, and includes a pair of adjustable ear rods or other patient contact. The system is configured to generate a laser beam from the laser, project the laser beam to a fixed location on the X-ray imaging detector, the fixed location associated with a Frankfurt plane of the patient, and adjust the patient support to have the patient contact aligned with the laser beam.

18 Claims, 9 Drawing Sheets

ALIGNING AN X-RAY MEDICAL IMAGING DEVICE USING THE FRANKFURT PLANE

TECHNICAL FIELD

Embodiments relate generally to systems and methods for x-ray medical imaging.

BACKGROUND

Systems that utilize high energy radiation, for example X-ray radiation, to examine the internal structure of an object are known. These systems may be used to produce images of body parts. Detection systems, particularly those used in medical applications, direct X-rays through the body part of interest toward an X-ray detector. In dental panoramic X-ray imaging, the image is captured during a process in which the X-ray generator and the imaging device move around the patient's head according to a predetermined geometric path and speed profile. The movement of the X-ray generator and the imaging device is traditionally synchronized so that the imaging device surface is perpendicular to the layer-of-interest.

SUMMARY

One object of some embodiments is to provide a mechanism for aligning or calibrating a patient support in an X-ray imaging system. The calibration techniques and systems described may be used in single modality imaging systems, for example, in a system that is designed for Cephalometric imaging only. However, the techniques and systems described may also be used in combination imaging systems, for example, a combination of Panoramic, Cephalometric, and/or Compute Tomography imaging modalities.

In one example, techniques and systems described help reduce drawbacks of Panoramic/Cephalometric/Computed Tomography (CT) combination imaging systems related to the calibration of critical components associated with the imaging systems. When, for example, an imaging system is modified or supplemented to allow for multiple types of images (for example, Panoramic, Cephalometric, and/or Computed Tomography (CT) images), the X-ray imaging system needs to be calibrated accurately in order to, for example, ensure accurate imaging and prevent multiple retakes of the images thereby preventing the patient from repeated X-rays and unnecessary exposure to X-ray radiation.

For example, as part of a Cephalometric imaging installation, correct alignment of the X-ray beam is important. In some instances, Cephalometric imaging components are provided as an add-on or accessory to systems that are designed for Panoramic imaging. Systems and methods described herein provide for the calibration of an imaging system capable of capturing Panoramic, Cephalometric, and/or Computed Tomography (CT) images of the patient. In some, but not all, systems there is a first X-ray source used for Panoramic and Computed Tomography imaging and a second X-ray source used for Cephalometric imaging. Systems and methods described herein provide, among other things, for marking, highlighting, and aligning to a Frankfurt plane associated with a patient by accurately positioning a Cephalometric patient support with respect to an X-ray detector using a laser beam projected from the X-ray source to a fixed location on the X-ray detector. In some systems, a specialized patient support (for example, a Cephalometric patient support) is not provided. Rather, a single patient support (which in some instances is used for multiple types of imaging) is provided. Techniques and systems disclosed herein may be used to calibrate these kinds of general patient supports too.

One embodiment includes an X-ray imaging system for medical imaging. The X-ray imaging unit includes a column. The X-ray imaging system also includes an upper shelf coupled to the column. The X-ray imaging system includes a rotating part rotatably coupled to the upper shelf and having a rotation axis with respect to the upper shelf. The rotating part includes an X-ray source, a laser, and an X-ray imaging detector. The X-ray source and the X-ray imaging detector are configured to provide an image by means of at least a rotational movement (R) of the rotating part. The X-ray imaging system also includes a Cephalometric patient support configured to support a patient to be imaged. The Cephalometric patient support is attached to the column by a first arm, and includes a pair of adjustable ear rods, wherein each of the ear rods has an ear bud. The laser is configured to generate and project a laser beam to a fixed location on the X-ray imaging detector, the fixed location associated with a Frankfurt plane of the patient. The Cephalometric patient support is adjustable to align the ear buds with the laser beam.

One embodiment includes an X-ray imaging system for medical imaging. The X-ray imaging system includes a first X-ray source, a laser, and an X-ray imaging detector. The X-ray imaging system also includes a patient support configured to support a patient to be imaged and attached to the X-ray imaging system by a first arm. The patient support includes a chin support, a nose support, pair of adjustable ear rods (each with an ear bud), or other patient contact. The laser is configured to project the laser to a fixed location on the X-ray imaging detector. The fixed location is associated with a Frankfurt plane of the patient. The patient support is adjustable to align the patient contact with the laser beam.

One embodiment includes a method for calibrating an X-ray imaging system including a column, a rotating part rotatably coupled to the upper shelf and having a rotation axis with respect to the upper shelf, the rotating part comprising an X-ray source, a laser, and an X-ray imaging detector. The method includes positioning the rotating part over a patient support attached to the column by a first arm. The patient support includes a patient contact, for example, a pair of adjustable ear rods, wherein each of the ear rods has an ear bud. The method also includes generating a laser beam from the laser disposed in source surface of the X-ray source facing the X-ray imaging detector. The method also includes projecting the laser beam to a fixed location on the X-ray imaging detector, the fixed location associated with a Frankfurt plane of the patient. The method also includes adjusting the patient support to have the patient contact aligned with the laser beam.

The method may also include positioning the rotating part to a first imaging configuration over a patient positioning means to provide one of a panoramic image and a computed tomography image. The method may also include while or during the step of providing one of a panoramic image and a computed tomography image, moving the rotating part by linearly moving the rotation axis with respect to the upper shelf, pivoting the upper shelf, and/or rotating the rotating part.

Another example embodiment includes a non-transitory computer-readable medium containing instructions that when executed by one or more electronic processors cause the one or more electronic processors to perform the actions associated with the method for calibrating an X-ray imaging system including a column, an upper shelf coupled to the column, a rotating part rotatably coupled to the upper shelf and having a rotation axis with respect to the upper shelf, the rotating part comprising an X-ray source, a laser, and an X-ray imaging detector. The method includes positioning the rotating part over a Cephalometric patient support attached to the column by a first arm. The Cephalometric patient support includes a pair of adjustable ear rods, wherein each of the ear rods has an ear bud. The method also includes generating a laser beam from the laser. The method also includes projecting the laser beam to a fixed location on the X-ray imaging detector, the fixed location associated with a Frankfurt plane of the patient. The method also includes adjusting the Cephalometric patient support to have the ear buds aligned with the laser beam.

The term "medical imaging" refers to, for example, dental, extra-oral, oral, maxillofacial, or ears, nose, and throat imaging.

Further embodiments are defined in dependent claims. The features recited in dependent claims are mutually freely combinable unless otherwise explicitly stated.

The definitions of the below-defined verbs and terms shall be applied, unless a different definition is given in the claims or elsewhere in this description/specification.

The verb "comprise" is used in this document as an open limitation that neither excludes nor requires the existence of un-recited features. The verbs "include" and "have/has" are defined as in the same manner as the verb comprise.

The terms "a", "an" and "at least one", as used herein, are defined as one or more than one and the term "plurality" is defined as two or more than two. The term "another", as used herein, is defined as at least a second or more.

The term "or" is generally employed in its sense comprising "and/or" unless the content clearly dictates otherwise.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed.

Figure 1A:
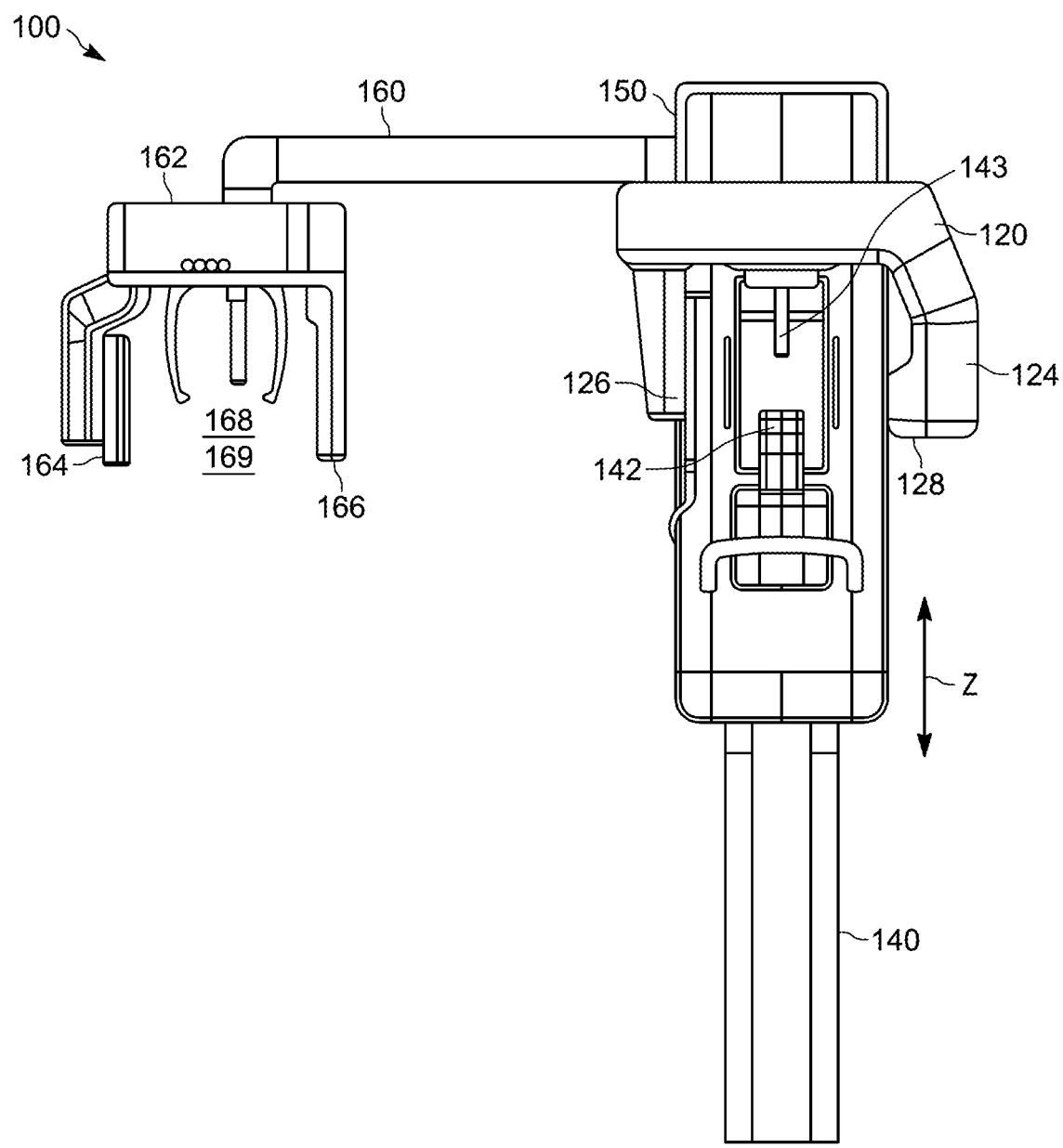
FIGS. 1A-1B illustrate a digital Panoramic/Cephalometric/CT combination system from the front and from above.
Figure 1B:
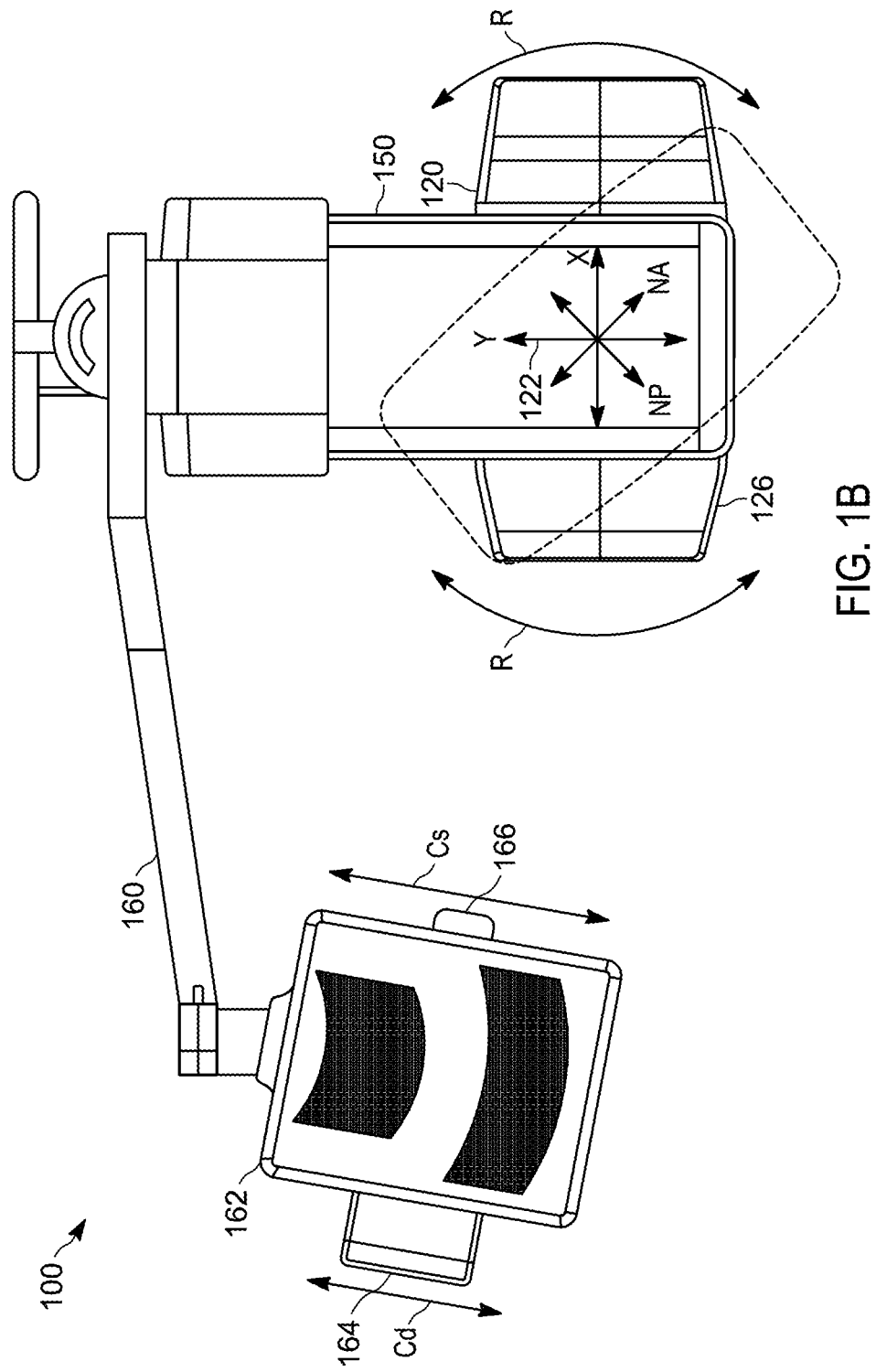

FIGS. 1A-1B illustrate a digital Panoramic/Cephalometric/Cone Beam Computed Tomography (CBCT) combination system 100 having, in the example provided, a column 140 that includes an up and down movement (denoted by "Z" in FIG. 1A) to adapt a height of the system 100 to a height of a patient for Panoramic, Cephalometric, and CBCT imaging modes.

An upper shelf 150 of the system 100 is attached to the column 140, for example, with a fixed joint. The upper shelf 150 supports a rotating part 120. The rotating part 120 (also known as a "gantry") has generally a form of a letter C and incorporates an X-ray source 124 on one end and an X-ray imaging detector 126 on the other end. The rotating part 120 rotates (denoted by "R" in FIG. 1B), for example, up to 400 degrees around a rotation axis 122. The X-ray source 124 is common for all the three imaging modes and an X-ray beam limiting device 128 is attached in front of the X-ray source 124.

The detector 126 may include either one or two detectors. In some embodiments, the detector 126 includes a Cephalometric detector (which also enables Panoramic imaging), one Panoramic/CBCT/Cephalometric combination detector, or one shot detector configured to be used in Cephalometric imaging. Some embodiments include two detectors. For example, the detector 126 may include a Cephalometric detector, which also enables Panoramic imaging, and a CBCT detector. There are several ways to attach the detectors with respect to each other and to change the particular detector that is located within an X-ray beam.

During imaging, the X-ray beam limiting device 128 controls a size and shape of the X-ray beam so that it matches requirements of a selected imaging mode, a selected image size, and the related detector size.

The rotating part 120 is connected to the upper shelf 150. The rotating part 120 is, in general, movable (at least one linear movement) so that the rotation axis 122 and, thus, a rotation center of the rotating part 120 with respect to the upper shelf 150 can be adjusted along a Y-axis (or line of movement) that is parallel to the upper shelf 150 during the imaging. Furthermore, the rotating part 120 is movable in a second linear direction (along an X-axis or line of movement) perpendicular to the first one so that the rotation axis 122 can be positioned within a plane defined by the linear movements X, Y.

In addition, there can be even a third N-movement that moves a fixing point of the rotation axis 122 with respect to the rotating part 120. Moving the rotation axis 122 along the X-ray beam NA may be used to change a magnification within the Panoramic and CBCT imaging modes. Moving the rotation axis 122 perpendicular to the X-ray beam NP enables a change between offset scanning and symmetrical scanning in the CBCT imaging, thus, affecting the Field Of View (FOV).

A Cephalometric arm 160 is used to attach a Cephalometric head 162 to the system 100. It has, for example, a dedicated X-ray imaging detector 164 at one end and a secondary collimator 166 at the other end. Between these two main parts 164, 166 hang Cephalometric patient positioning support parts 168, 169, which consist of adjustable ear rods 168 and an adjustable nose (nasion) support 169. The patient's head is supported from an outer part of an ear canal with the ear rods 168 and from a nose using the corresponding adjustable nose support 169.

The Cephalometric X-ray detector 164 is attached to the head 162 with a $C_d$-movement that moves the detector 164 perpendicularly to the X-ray beam. Alternatively, it is possible to perform the Cephalometric imaging by a one shot technique, when the detector 164 is sufficiently large.

The Cephalometric secondary collimator 166 is also attached to the head 162 with a $C_s$-movement that is parallel to the $C_d$-movement and, thus, also perpendicular to the X-ray beam.

The support parts 168, 169 are attached to the head 162 in a manner that enables them to rotate to two main imaging positions: the lateral and posterior anterior (PA) projections. The lateral projection is basically a side view and the PA projection is from a back-to-front view of a skull.

For Panoramic and CBCT imaging, a patient is typically supported by means of a lower shelf 142 and possibly also by means of a temple support 143. The support points or patient contacts are, for example a tip of a chin and a forehead or temple of a patient.

The Panoramic imaging system 100 uses the rotation R and linear X-, Y-, or both X- and Y-movements during the scan resulting in a Panoramic image. Furthermore, depending on the sensor technology used, the image is clocked out using Time Delay Integration (TDI) or full frame read-out mode of the detector. The Panoramic (sharp) layer is defined by the velocities of the movements and, in the case of TDI, the readout rate of the Panoramic detector. When using a full frame detector, the final shape of the layer is calculated on the computer after the scan. The rotation angle is, for example, about 270 degrees.

In the system 100, CBCT imaging is, for example, implemented by using a rotation movement R and reading out the CBCT detector with a fill frame mode. Thus, projection X-ray images of the Region of Interest (ROI) are, for example, produced in a way that the center of the ROI and the rotation movement R coincide. The effective rotation angle (aperture) ranges, for example, from approximately 180 degrees to 360 degrees depending on the system 100.

In Cephalometric imaging, the patient is supported by patient positioning structures 168, 169 located at the Cephalometric head 162 of the system 100. The X-ray beam is arranged to scan the patient's head with a combination of rotation R and linear Y-movement. The X-ray beam is then further collimated by the secondary collimator 166 and finally captured by the Cephalometric detector 164, which both move in synchronism with the X-ray beam.

Figure 2A:
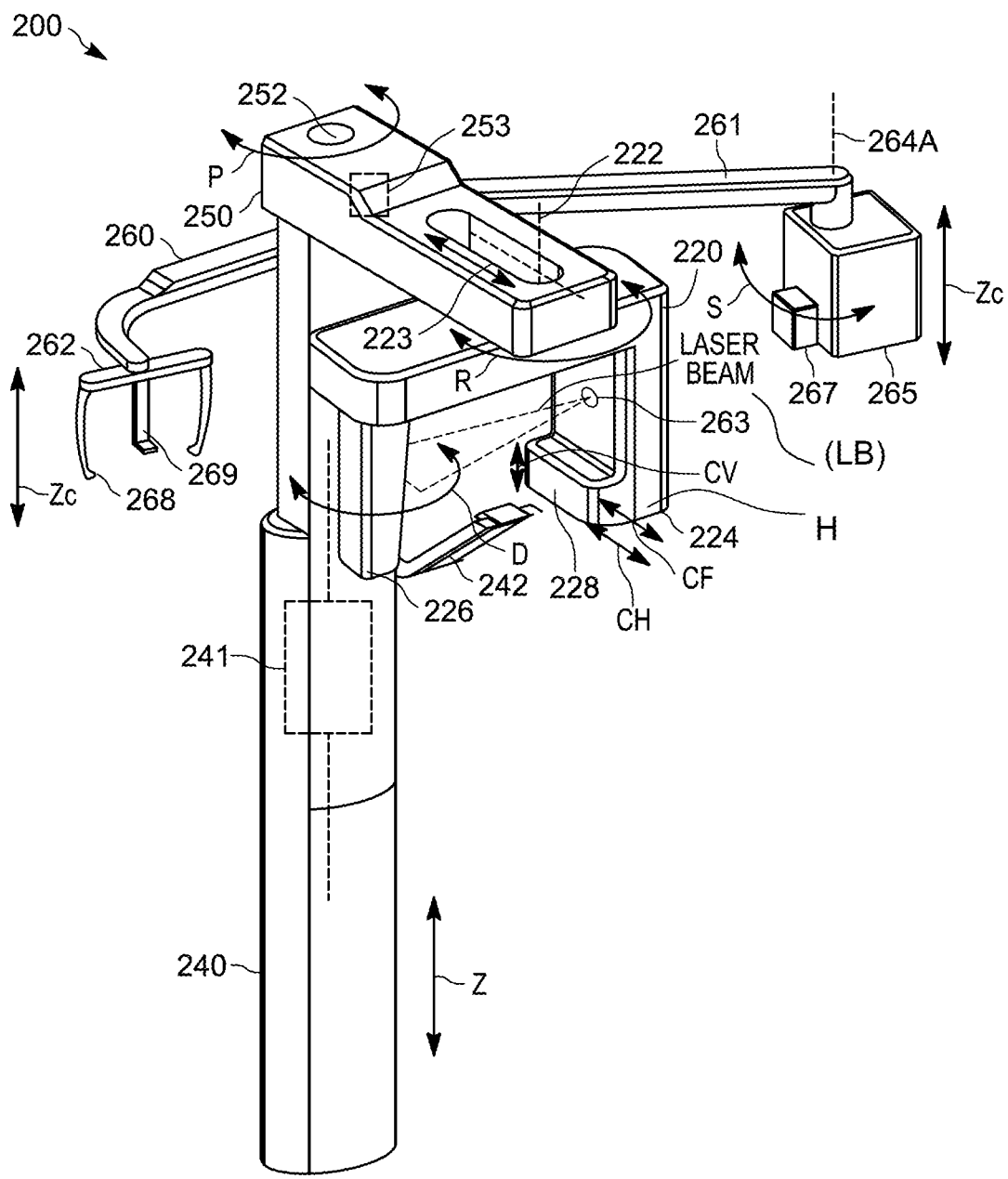
FIG. 2A illustrates an X-ray imaging system for a medical imaging and its main parts and movements.

FIG. 2A illustrates main parts of an X-ray imaging system 200, which can be used in medical imaging, for example, in extra-oral dental imaging.

The system 200 includes a rotating part (gantry) 220, which includes a first X-ray source 224. An X-ray imaging detector 226 is also attached to the rotating part 220. A position of the X-ray imaging detector 226 is adjustable, for example, the X-ray imaging detector 226 is rotatable or movable in a linear fashion. The X-ray source 224 and/or the X-ray imaging detector 226 provides, for example, a Panoramic, CT, or Cephalometric image by means of at least a rotational movement R around a rotation axis 222 of the rotating part 220. The R-movement of the rotating part 220 is, for example, up to 400 degrees around the rotation axis 222. In the example illustrated, the first X-ray source 224 is positioned within a housing H and the housing H also includes a laser 263 that is positioned so that a laser beam LB generated by the laser 263 impinges the surface of the X-ray imaging detector 226 that faces the X-ray source 224. The laser 263 is configured to generate the laser beam LB and project the laser beam LB to a fixed location on the X-ray imaging detector 226 (shown in FIG. 2D). The laser 263 may be mounted within an adjustment mechanism, for example, one or more electric motor driven devices that are configured to move the laser 263 so that the laser beam LB may be directed at a desired location, for example, the fixed location of the X-ray imaging detector 226. The electric motors may be controlled by a controller, discussed in greater detail below.

The system 200 also includes a second X-ray source 265 attached to a column 240 by a second arm 261. The second X-ray source 265 includes an X-ray beam limiting device 267. Although described as two separate arms, the first arm 260 and the second arm 261 may be mechanically linked so as to operate in effect as a single arm. The single arm may be pivotally connected to the column 240 so that raising one end of the single arm causes the other end of the single arm to lower (for example, in a manner similar to a seesaw or teeter-totter).

The rotating part 220 includes a rotating motor, which is configured to rotate the rotating part 220 by means of rotation means (not shown). Alternatively, the rotating motor can be situated in an upper shelf 250 of the system 200. In one example, the rotating part 220 is attached to the upper shelf 250.

The rotating part 220 has, for example, a form approximating a letter C and the X-ray source 224 is on one end of the rotating part 220. The X-ray source 224 is common for two imaging modes—Panoramic imaging and CT imaging, for example, CBCT imaging, where an X-ray beam is a cone-shaped beam. In some CT imaging techniques, the X-ray beam is one of a pyramidal-shaped beam, half-moon-shaped cone beam, or other shaped beam.

In the example provided, the X-ray source 224 also includes a beam limiting device 228 for the X-ray source 224 and an X-ray beam limiting motor configured to adjust the X-ray beam limiting device 228. During imaging, the X-ray beam limiting device 228 controls the size and shape of the X-ray beam so that it matches the needs of a selected imaging protocol, a selected image size, and the related detector size.

Figure 2B:
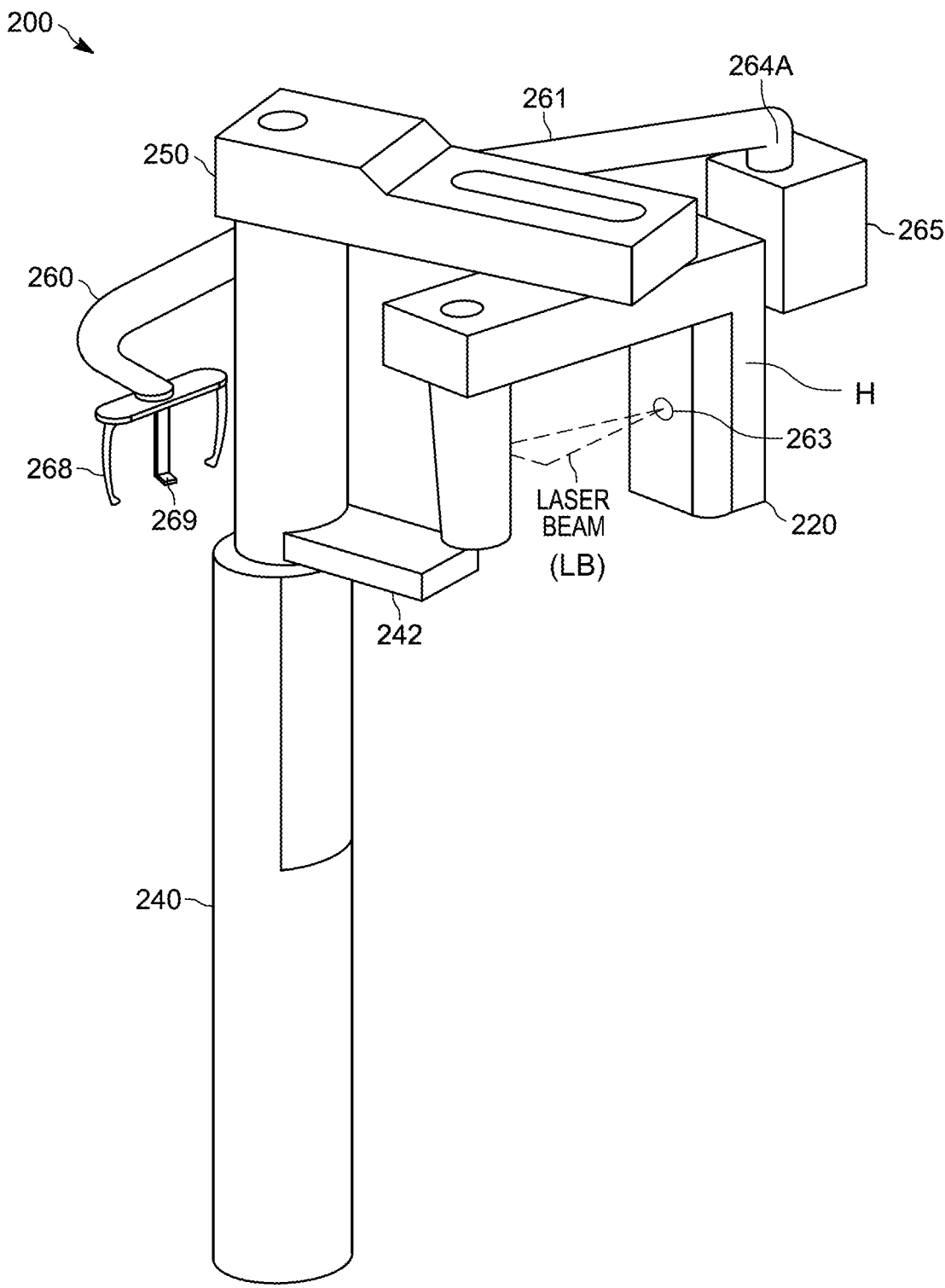
FIG. 2B illustrates an X-ray imaging system and a patient in a Panoramic/CT imaging position during an imaging.
Figure 2C:
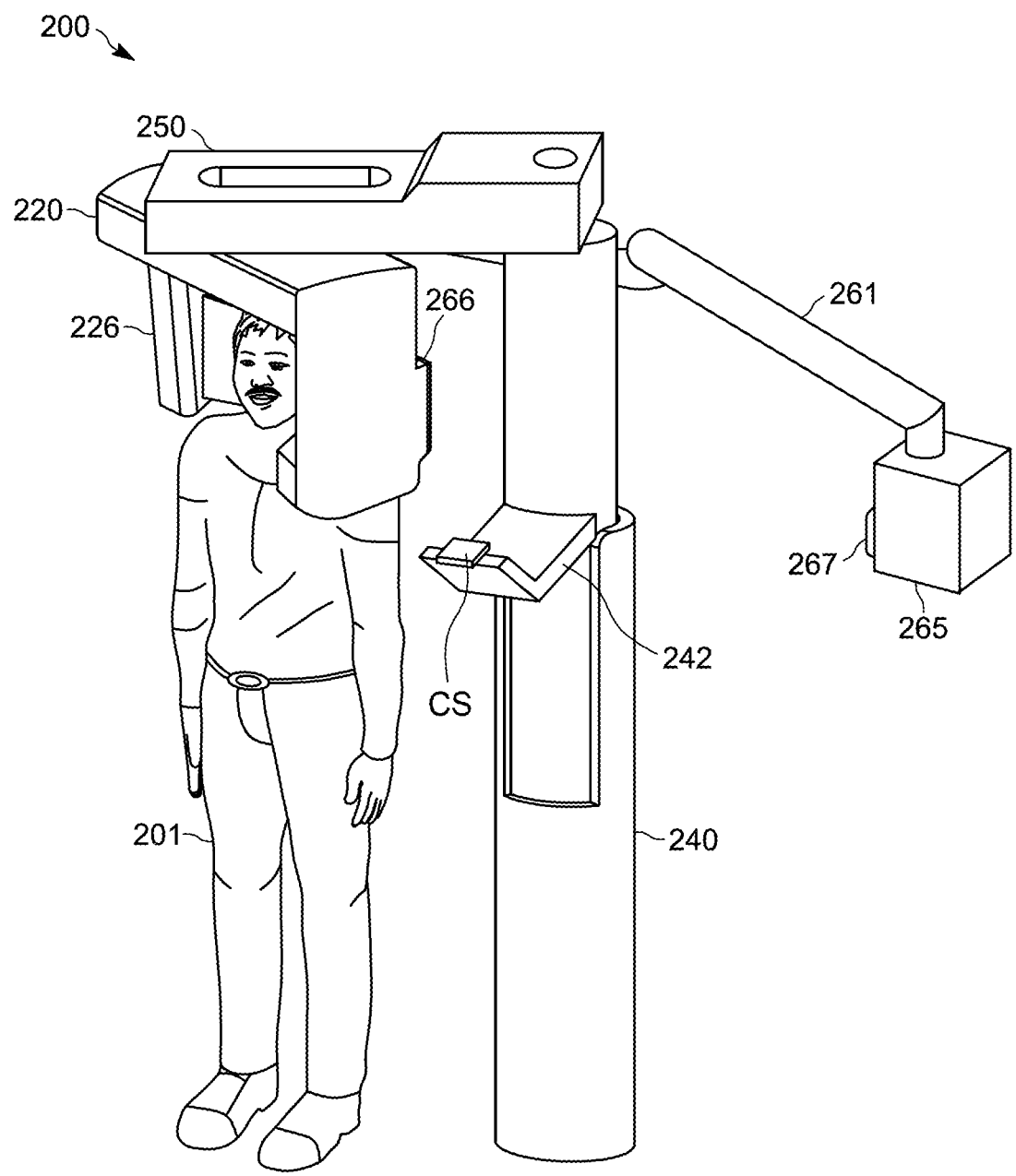
FIG. 2C illustrates an X-ray imaging system and a patient in a Cephalometric imaging position during an imaging.
Figure 2D:
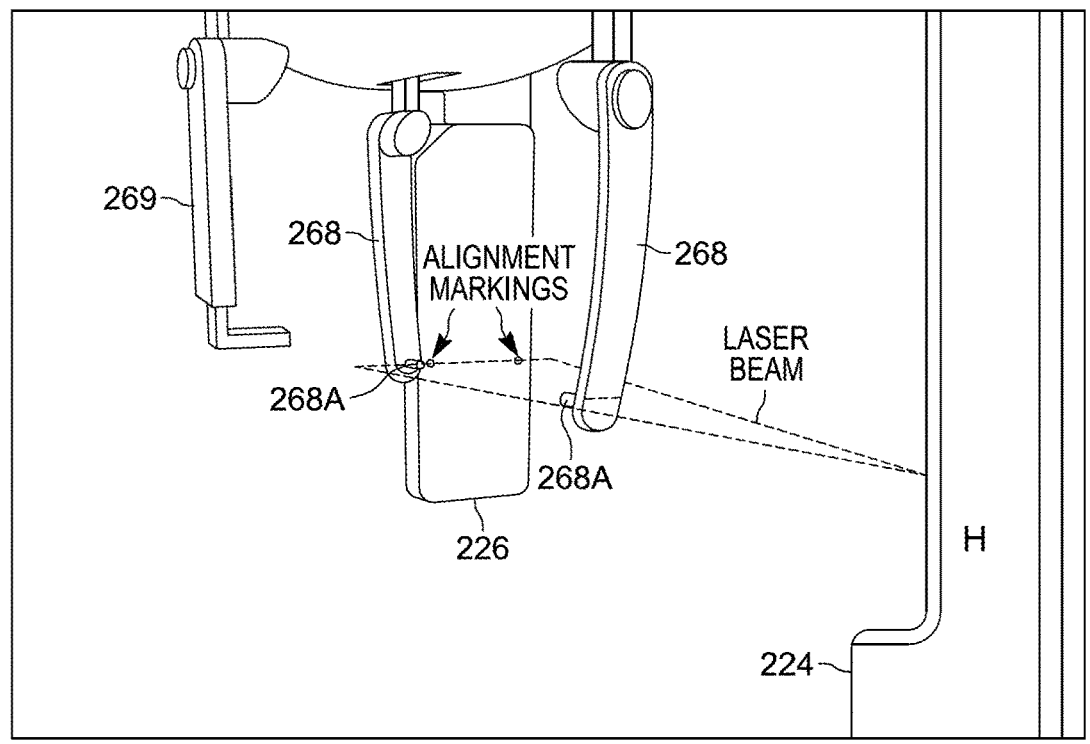
FIG. 2D illustrates a calibration of a Cephalometric patient support placed between an X-ray source and an X-ray detector.
Figure 2E:
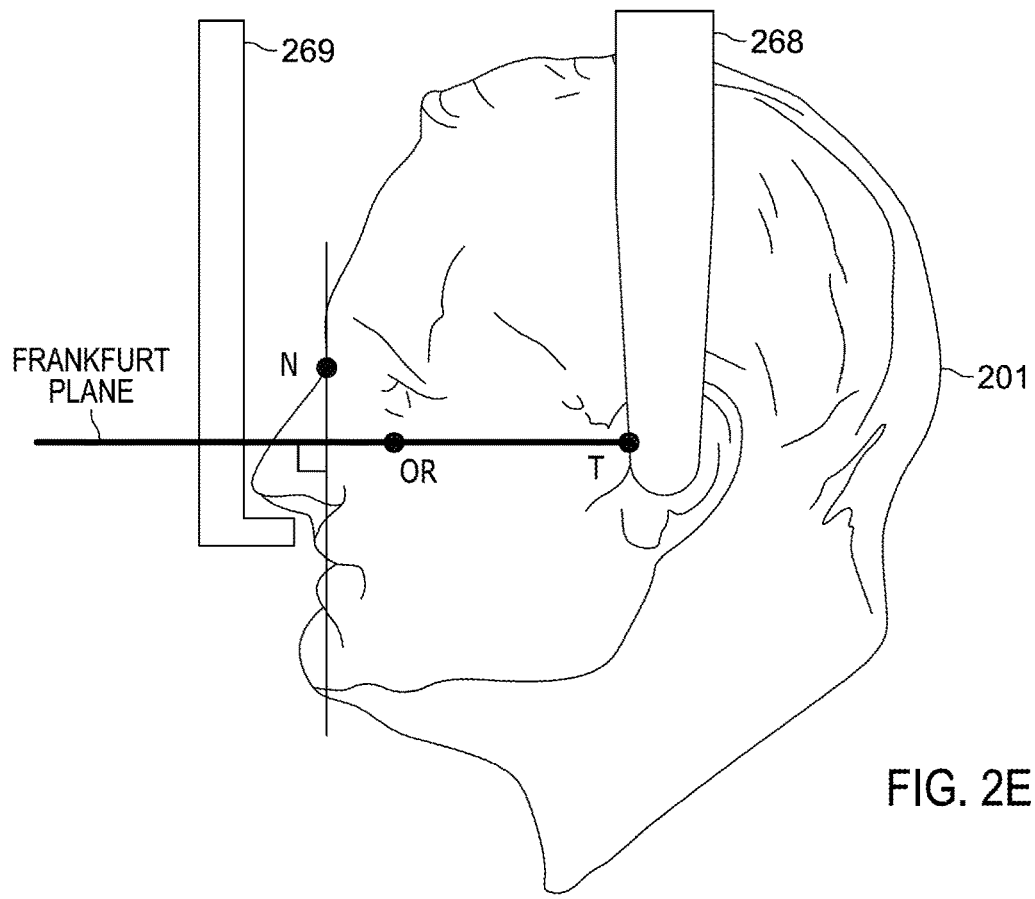
FIG. 2E is a side view of a patient illustrating a Frankfurt plane of the patient.
Figure 2F:
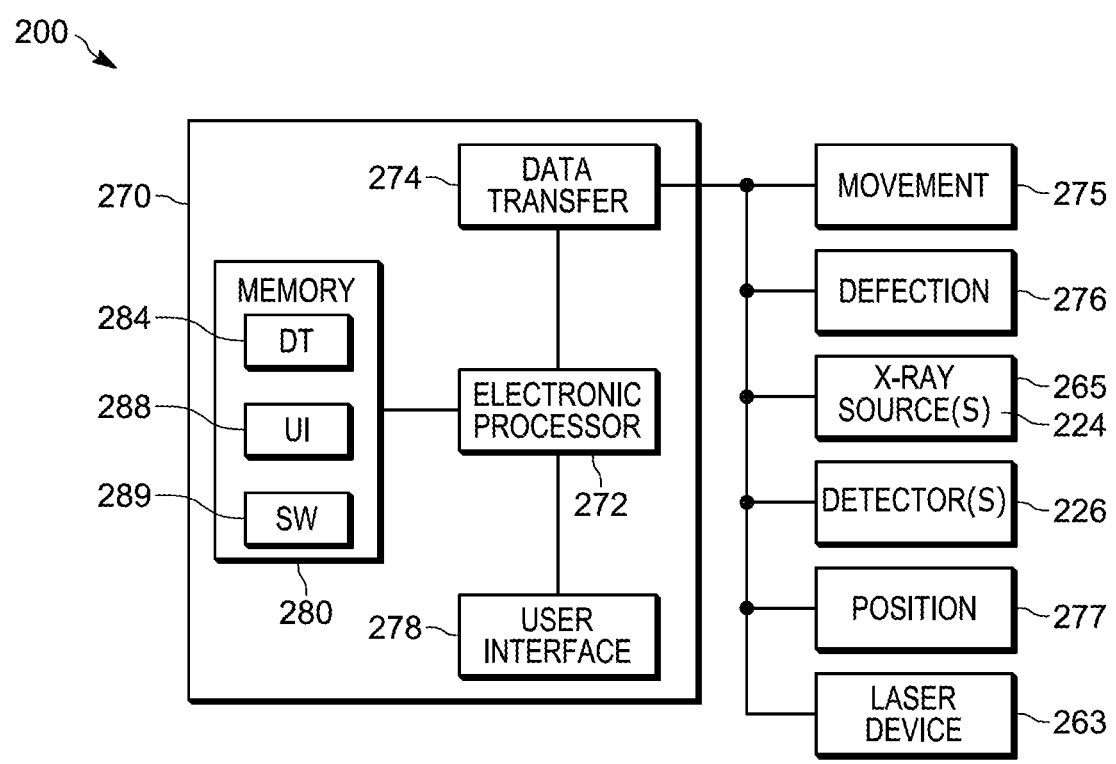
FIG. 2F illustrates functional elements of the X-ray imaging system.
Figure 2G:
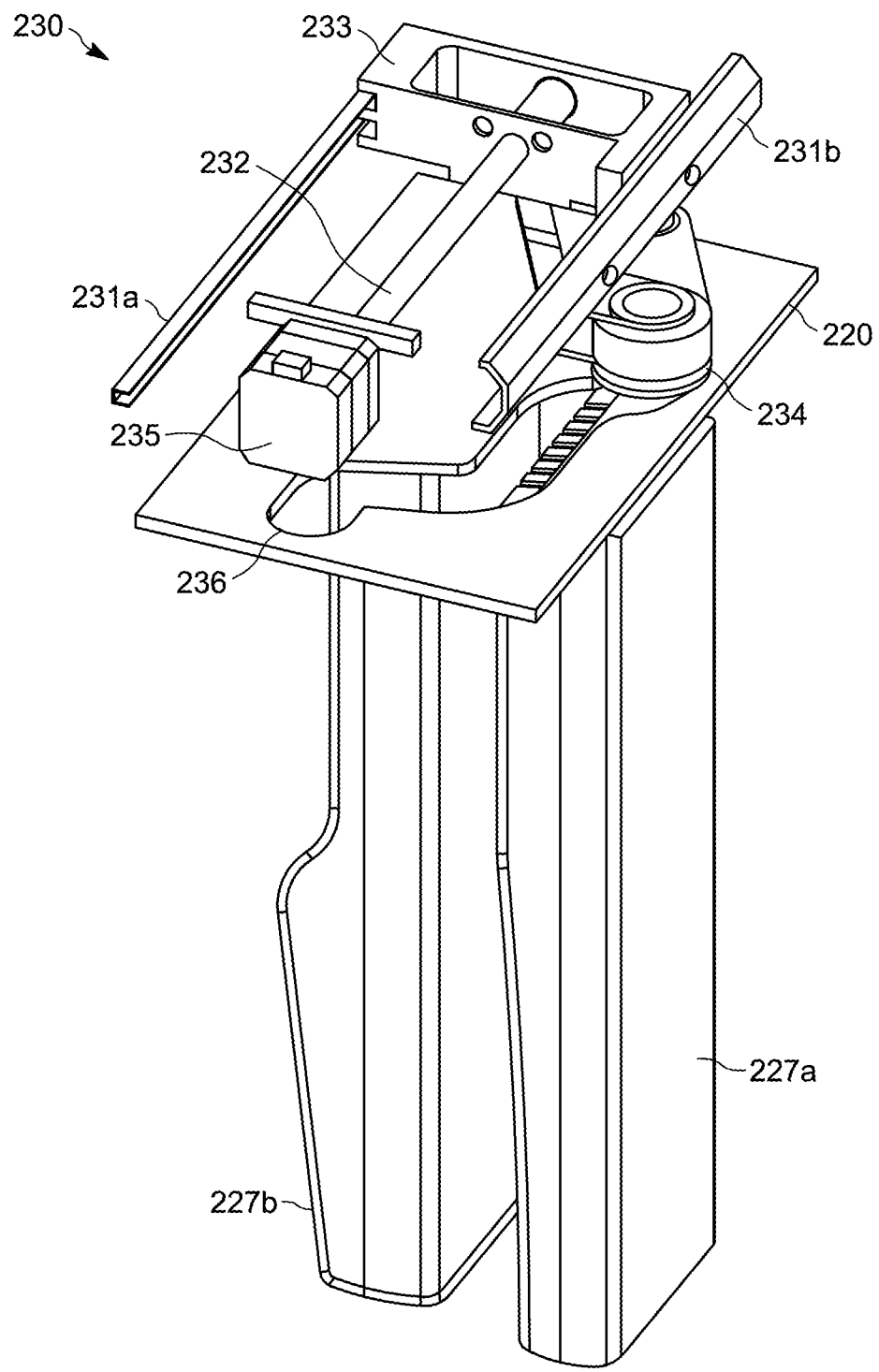
FIG. 2G illustrates an exemplary embodiment of a two detector X-ray imaging unit, exemplarily configured in a Panoramic imaging position.

On the other end of the rotating part 220 is the X-ray imaging detector 226, which can include, for example, one or two X-ray detectors 227a, 227b (see FIG. 2G). An example embodiment of a one-detector X-ray imaging detector 226 can include one X-ray detector 227 which may include one Panoramic detector, one Cephalometric detector, which also enables Panoramic imaging, one Panoramic/CT combination detector, one Panoramic/CT/Cephalometric combination detector, or one detector configured to be used in Panoramic/CT imaging and in one-shot Cephalometric imaging.

The one-detector X-ray imaging detector 226 can be adjustable, for example, by rotating the X-ray imaging detector 226 relative to the rotating part 220 so that one detector of the X-ray imaging detector 226 can be positioned preferably perpendicularly to the used X-ray source 224 or 265 (described in further detail herein) and/or by moving one detector of the X-ray imaging detector 226 in a linear fashion relative to the rotating part 220 for adjusting a distance between the one detector or X-ray imaging detector 226 and the X-ray source 224 in Panoramic/CT imaging.

In an example of a two-detector X-ray detector 226, the detector 226 can include one Panoramic detector and one CT detector, or one Cephalometric detector, which also enables Panoramic imaging. In a two-detector embodiment of the detector 226, the detectors are arranged, for example, successively in Panoramic imaging, whereupon the Panoramic or Cephalometric detector is arranged as a front detector for arranging magnification ratio for the imaging mode, and the CT detector as a rear detector. The swap of the detectors 227a, 227b (see FIG. 2G) is arranged so that the front detector 227a moves aside by means of moving means 230, for example, a rail 231a, 231b and a rotator configured to move along the rail 231a, 231b and to rotate so that the front detector 227a slides, for example, next to a rear detector 227b, when it is necessary to use the rear detector 227a in CT imaging or the front detector 227a in Cephalometric imaging. Alternatively, the front detector 227a can be moved to another position relative to the rear detector 227b in Cephalometric imaging. The place of the front detector 227a in Cephalometric imaging may depend upon on how the front detector 227a is displaced by means of the swap movement, and the R- and L-movements relative to the X-ray source 265 that is used. The Cephalometric detector 227a can be positioned preferably perpendicularly to the used X-ray source 265. The front detector 227a returns similarly by sliding, when it is necessary to move the front detector 227a back to the front position.

The rotating part 220 can include a detector motor 235 configured to move at least one detector by means of the moving means 230, if the detector 226 includes separate detectors 227a, 227b for the Panoramic and CT imaging.

The system 200 includes the column 240 for adapting a height Z of the system 200—and the rotating part 220. The column 240 includes height adapting means 241 which may include, for example, a height motor, a gear, and a threaded rod, and telescopic or counter weighted means configured to be driven by the height motor, for providing an up/down movement Z to adapt the height of the rotating part 220 to the height of the patient 201 for the Panoramic, Cephalometric, or CT imaging modes. The height adapting means 241 can realize the Z-movement, for example, as a movement of the height adapting means and/or as a telescopic or counterweighted movement.

A lower shelf or second patient support 242 is attached to the column 240. The lower shelf or second patient support 242 is used for positioning a patient 201 for imaging, for example, Panoramic and/or CT imaging and for supporting the patient 201, for example, from a tip of the patient's 201 chin by a chin support CS during the imaging. In some cases, the system 200 may only include one patient support, for example, the lower shelf or second patient support 242.

Alternatively, when the system 200 includes a seated patient's 201 positioning system (not shown), the Z-movement is realized, for example, by adapting in the Z-direction the height of at least one of the following: a chair, the lower shelf 242, and the column 240.

The lower shelf 242 can also include a head support (not shown), which supports, for example, the patient's 201 forehead and/or temple in the Panoramic/CT imaging position.

The system 200 includes the upper shelf 250, which supports the rotating part 220. In one example, the upper shelf 250 is attached to an upper end of the column 240 with a pivoting joint (means) 252, which enables a pivot movement P of the upper shelf 250 around the column 240 and in respect to a lower shelf 242 so that the rotating part 220 is over, for example, the lower shelf 242.

The upper shelf 250 includes pivot movement means 253, which includes, for example, a pivot motor 253 configured to pivot the upper shelf 250 around the column 240 by means of the pivoting joint 252.

The upper shelf 250 includes linear movement means 223, for example, a linear conveyor configured to support the rotation means of the rotating part 220 and to enable the rotating part 220 to rotate around the rotation axis 222, at least one rail and/or track configured to guide the linear conveyor in the upper shelf 250, and a linear motor configured to drive the linear conveyor along the at least one rail and the upper shelf 250, which enable the rotating part 220 and the rotation means to move with respect to the upper shelf 250 by means of a linear movement L. The linear movement means 223 of the upper shelf 250 can be provided so that L movement in a plane of the upper shelf 250 is a direct linear movement, for example, it is parallel to the upper shelf 250 or it is in a certain angle with respect to the parallel direction, or the L-movement in the plane of the upper shelf 250 is a non-direct linear movement having for example a curved path or a devious path.

The rotation means attach the rotating part 220 to the upper shelf 250. The rotation means are able to move with at least one L-movement so that the axis 222 and, thus, the rotation center in respect to the upper shelf 250 can be adjusted along the L-movement. Thus, the axis 222 can be positioned within a plane defined by the P-movement of the upper shelf 250 and the L-movement of the rotating part 220 during the imaging.

By using a rotating P-movement, rather than a linear X-movement, to adjust the lateral position of the rotating part 220, it is possible to design a lighter and thinner upper shelf 250, thus giving the system 200 a smaller footprint. In contrast, the conventional method of relying on a linear X-movement requires a wider upper shelf 250, and relying on an NP-movement requires a wider rotating part 220, as depicted in FIG. 1b.

In some cases, the X-ray source 224 on the one end of the rotating part 220 weighs more than the detector 226 on the other end. As a result, a movement of the center of the gravity of the rotating part 220 can cause a varying load to a joint construction (not shown) of the rotating part 220, which includes the linear movement means 223, so that the rotating part 220 wobbles during the imaging and, thus, reduces image quality.

In order to reduce these problems, the upper shelf 250 includes a controlling arrangement (not shown) that enables the R-movement of the rotating part 220 in relation to the upper shelf 250 so that the axis 222 travels substantially with the center of the gravity of the rotating part 220, which, in turn, stays in a neutral axis of the joint construction of the rotating part 220 during imaging. A virtual rotation axis of the rotating part 220 is achieved by synchronizing R-, L-, and P-movements during the scanning.

The controlling arrangement, by operating the rotating part 220 in the manner described above, reduces torque applied to the joint construction and increases image quality by removing artifacts caused by wobbling.

In addition, the controlling arrangement enables a lighter, cheaper, and thinner structure of the rotating part 220 and its joint construction In addition, the system 200 includes on one side of the column 240 a first Cephalometric arm 260 that has a certain first length. The arm 260 attaches a Cephalometric patient support 262 to the system 200 at a certain first distance that corresponds with the first length from the column 240.

The Cephalometric patient support 262, which has a significantly simpler structure than in traditional Cephalometric units, includes Cephalometric patient support means 268, 269, for example, two adjustable ear rods 268 and an adjustable nose (nasion) support 269, for supporting the patient 201 to be imaged. The patient's head is supported, for example from an outer part of the ear canal with the ear buds 268A (shown in FIG. 2D) included in the ear rods 268 and from the nose using the nose support 269. The adjustable ear rods 268 and adjustable nose support 269 is attached to the Cephalometric patient support 262 in a manner that enables them to rotate, for example, two main imaging positions: lateral and PA projections. The lateral projection is basically a side view and the PA projection is from back to front view of a skull of the patient.

The ear rods 268 can be tiltable or rotatable ear rods having a down position, where the ear rods 268 support the patient 201, and an up position, where it is possible to place the patient in the Cephalometric imaging position or where the patient can depart from the Cephalometric imaging position, when the tilted or rotated ear rods 268 in the up position provide a clear passage of the patient.

In addition, the system 200 may include on other side of the column 240 a second Cephalometric arm 261 that has a certain second length. Attached to the second Cephalometric arm 261 is a second X-ray source 265, which is used in Cephalometric imaging. The second Cephalometric arm holds the second x-ray source at a second distance from the system 200, corresponding to a second length from the column 240. The X-ray source 265 includes an X-ray beam limiting device 267 for the Cephalometric imaging. Optionally, the X-ray beam limiting device 267 can be attached to the X-ray source 265. The X-ray source 265 can be configured to rotate around a rotation axis 264 by means of rotation means 264A configured to perform a scanning movement S. The axis 264 of the X-ray source 265 is in line with a focal spot of the X-ray source 265 so that it passes through the focal spot. The arm 261 or the X-ray source 265 includes a rotating motor, which is configured to rotate the X-ray source 265 around the axis 264, which coincides with the focal spot of the X-ray source 265.

As noted, in some embodiments, the arms 260, 261 can be separate arms attached to the column 240, or it is possible to use one arm 260, 261, which includes the Cephalometric head 262 in its one end and the X-ray source 265 with the X-ray beam limiting device 267 in the other end of the single arm 260, 261.

In addition, the rotating part 220 can include a Cephalometric (secondary) collimator 266, which is used in the Cephalometric imaging together with one detector of the detector 226. The Cephalometric collimator 266 is attached, for example, to one (right) side of the rotating part 220 (for example, X-ray source 224), as depicted in FIG. 2C. Alternatively, the Cephalometric collimator can be attached, for example, to another (left) side of the rotating part 220 (for example, X-ray source 224).

In addition, the rotating part 220 can include a detector motor 235 configured to rotate at least one detector of the detector 226 for the Cephalometric imaging, and a collimator motor configured to adjust a position (height) of the Cephalometric collimator 266 in the Z-direction and/or a position of the collimator of the X-ray source 224. Alternatively, or in addition, the X-ray beam limiting motor or the collimator motor can be configured to adjust both the X-ray beam limiting device 228 and the Cephalometric collimator 266.

The rotating part 220 is driven over the Cephalometric head (support) 262, for example, with the P-, R-, and L-movements, so that the detector 226 and the Cephalometric collimator 266 are positioned for Cephalometric imaging.

The X-ray source 265 can be configured to provide, together with, for example, the detector 226 (for example, the Cephalometric detector 227a attached to the detector 226) and the Cephalometric collimator 266 in the rotating part 220, a Cephalometric image from the positioned patient 201, when it is rotated around the axis 264 by means of the S-movement, and the detector 226 and the Cephalometric collimator 266 are arranged to move, for example, by means of at least one of the P-, R-, and L-movements of the rotating part 220. Alternatively, the scanning movement of the X-ray beam—for example, a linear S-movement can be performed by moving the X-ray beam limiting device 267 of the X-ray source 265.

If the one-shot detector is used, the detector 226 and the Cephalometric collimator 266 are positioned by means of at least one of the P-, R-, and L-movements, but the image can be taken without these movements and/or without the S-movement.

Thus, there is no need for a dedicated holder or the $C_s$-movement for the detector 164 and the $C_d$-movement of the Cephalometric collimator 166, when the scanning movement is executed with, for example, the P-, R-, L-, and S-movements.

The arms 260, 261 can be arranged so that a height of the Cephalometric head 262 with the ear rods 268 and nose support 269 is fixed relative to the X-ray source 265.

However, the fixed height may cause problems, because an anatomy of patients 201 varies for example, the vertical distance where ear openings are located compared to patient's 201 shoulders differs significantly from one patient 201 to another. Thus, either the patient 201 is located too low in the resultant Cephalometric image, showing only upper vertebras, or the patient 201 is located so high in the images that the shoulder of the patient 201 touches the detector 226, which is a problem especially with a scanning. Furthermore, the preferred Cephalometric imaging geometry requires that the focal spot and the tips of the ear rods 268 are at the same (horizontal) axis.

In to reduce these problems, variable length ear rods 268 can be used while keeping the arms 260, 261 fixed height relative to each other.

Alternatively or in addition, in order to eliminate these problems, the system 200 can include Cephalometric height adjusting means (not shown) that are configured to independently adjust the height—in respect to the column 240—of the arms 260, 261 that support the Cephalometric head 262 at the one end and the X-ray source 265 on the other end.

When the operator has adjusted the height of the arms 260, 261 by means of an up/down $Z_c$-movement, the focal spot follows the tips of the ear rods 268 automatically and, thus, the geometry (ear rod tip to focal spot line) remains intact. Yet, the detector 226 and the Cephalometric collimator 266 on each side of the patient 201 take their height from the column 240 and, thus, are on a different height in respect to the ear rods 268 and the patient 201 than before the adjustment.

The Cephalometric height adjusting means provides a way to adapt an exposed area to a given anatomy of the patient 201 by enabling an operator (user) to adjust the height of the patient 201 without compromising the geometry.

Since the first and second X-ray sources 224, 265 can be arranged at different heights with respect to the column 240 in the Z direction by means of the height adapting means 241 and/or the Cephalometric height adjusting means, it is possible to position the patient 201 without any additional adjustment of the Cephalometric head 262 in the Z direction as it is needed when using the X-ray source 224 of the rotating part 220 for the Cephalometric imaging.

The movements of system 200 are simple, because the traditional X-movement as well as the $C_d$- and $C_s$-movements of the detector 226 and the secondary collimator 266 in the Cephalometric head 262 are replaced by using the P-movement instead. The movements are carried out using the L-movement and the P-movement of the upper shelf 250.

In addition, by using the P-movement, the structure of system 200 is made simpler and cheaper, because the Cephalometric imaging can optionally be implemented by using only one "non-detachable" detector 226. This reduces the risk of breaking the detector 226 because there is no need to remove it from a holder of the rotating part 220 to detach it from a holder of the Cephalometric head 262 when changing the imaging mode from the Panoramic/CT mode to the Cephalometric mode. The detector for Panoramic imaging in the detector 226 can be rotated from the Panoramic imaging position to the Cephalometric imaging position so that it is possible to use the same detector in both Panoramic and Cephalometric imaging.

In addition, the structure of system 200 provides a simple workflow when, for example, the change from the Panoramic/CT mode to the Cephalometric mode—the movement of the rotating part 220 from the Panoramic/CT imaging position to the Cephalometric position without changing the detector 226 from one holder to other holder—is automated, thus decreasing both the amount of manual work required and the time needed for the work flow.

It is also possible that the system 200 includes the upper shelf 250 that pivots around the column 240 and the rotating part 220 that is configured to be positioned by means of the above-described L- and P-movements for providing the Panoramic and/or CT imaging, but has a more conventional Cephalometric head 262 comprising the Cephalometric detector, the secondary collimator, and the patient positioning support parts.

Cephalometric imaging is provided by means of the X-ray source 224 of the rotating part 220, and the secondary collimator and the Cephalometric detector of the Cephalometric head 262. The X-ray source 224 is arranged to scan the patient's 201 head with the R- and L-movements. The X-ray beam is collimated by the secondary collimator and captured by the Cephalometric detector, which are synchronized with the X-ray beam.

It is also possible that the system 200 is provided so that it includes only one X-ray source, which has several positions for providing the Panoramic, CT, and Cephalometric imaging. The one X-ray source is positioned relative to the rotating part 220 during the imaging.

FIG. 2B illustrates a positioning of the patient 201 during Panoramic/CT imaging. The patient 201 is supported by the lower shelf 242 and possibly to the head support of the system 200 in a Panoramic/CT imaging position, where the rotating part 220 is over the lower shelf 242.

If the upper shelf 250 as well as the rotating part 220 are in a different position than the Panoramic/CT imaging position—in a Cephalometric imaging position or in an intermediate position between, for example, the Panoramic/CT and Cephalometric imaging positions—the upper shelf 250 is moved from that position to the Panoramic/CT imaging position by the P-movement and, then, the rotating part 220 is further adjusted by the R- and L-movements so that the rotating part 220 is ready for the Panoramic/CT imaging.

In addition, the rotating part 220 can have a patient positioning position, where the X-ray source 224 or the detector 226 are out of the way and do not interfere with the positioning of the patient 201 to the Panoramic/CT and/or Cephalometric imaging positions when the rotating part 220 is over the lower shelf 242 or the Cephalometric head 262. The patient positioning position can be accomplished by the R-movement so that the rotating part 220 is rotated to such position, where it is possible to place the patient 201 to the Panoramic/CT and/or Cephalometric imaging positions or to remove the patient 201 by moving the patient's 201 head between the X-ray source 224 and the detector 226. Alternatively, it is possible to realize the patient positioning position by means of the P-movement, whereupon the whole rotating part 220 is moved away from the Panoramic/CT and/or Cephalometric imaging positions, when the patient 201 is positioned.

The positioned X-ray source 224 and the detector 226 are configured to provide a Panoramic image when the rotation axis 222—a rotation center of the rotating part 220—is positioned by at least one of the P- and L-movements.

Depending on the sensor technology used, the image can be clocked out using a TDI mode or a full frame read-out mode of the detector. In the TDI mode, the image is read out one column at a time, whereas in the full frame mode, the image is read out whole image frame at a time. The Panoramic (sharp) layer is defined by the velocities of the movements and, in the case of TDI, the readout rate of the Panoramic detector. When using a full frame detector, the final shape of the layer is calculated on the computer after the scan. Rotation angle is, for example, about 270 degrees, but this is not intended to be limiting.

During CT imaging, the patient 201 is also supported by the lower shelf 242 and possibly by the head support of the system 200 in the Panoramic/CT imaging position. The X-ray source 224 and the detector 226 are configured to provide a CT image when the detector 226 is attached to the rotating unit and the rotation center of the rotating part 220 is positioned so that it can coincide with the ROI.

The positioned X-ray source 224 and the detector 226 are configured to provide a CT image, for example, CBCT image, when the detector 226 is attached to the rotating part 220, and the rotation axis 222 is positioned by at least one of the R-, L-, and P-movements during the CT imaging.

When the system 200 is used with a symmetric imaging geometry, CT imaging can be carried out by using only the R-movement and reading out the CT detector in a full frame mode. Alternatively, or in addition, CT imaging can be carried out by using the P-, R-, and L-movements, using the controlling arrangement in the upper shelf 250, for positioning the virtual rotation axis of the rotating part 220 so that it coincides with the ROI. Thus, projection X-ray images of the ROI are produced in a way that the center of the ROI and the R-movement coincide. In one embodiment, the effective rotation angle (aperture) ranges, for example, from approximately 180 to 360 degrees depending on the system 200.

When the system 200 is used in an offset imaging, CT imaging can be carried out by scanning the image by using the R-, L-, and P-movement. By driving these R-, L-, and P-movements in synchronism, the effective center of the rotation can be deflected to the side of the X-ray beam and, thus creating an offset geometry. Offset scanning can be provided by a first "solid" offset geometry and a full 360 degree rotation of the CT detector.

Alternatively, the offset scanning can be provided by a second offset geometry, where the patient 201 is imaged by scanning an essentially maximal first imaging offset with approximately 180 degree rotation of the detector in a first imaging direction. Then, the detector is displaced to the other side of the rotation center to obtain an essentially maximal second imaging offset by approximately 180 degree rotation of the detector in a second imaging direction, which is opposite to the first direction. Alternatively, the detector is rotated to the starting position, displaced to the other side of the rotation center, and, then, scanning the essentially maximal second imaging offset by approximately 180 degree rotation in the first direction.

Alternatively, offset scanning can be provided by a third offset geometry, where the patient 201 is imaged by a first imaging offset, where the edge of the X-ray beam area touches the rotation center, and by 360 degree rotation of the detector. Next, the detector and the X-ray source 224 are displaced parallel in such a way that the X-ray beam area moves away from the rotation center so it hits or slightly overlaps the previously imaged area. Then, the detector is rotated 360 degrees for completing a second imaging offset.

The system 200 provides same versatility in the CT imaging geometry by means of the R-, L-, and P-movements instead of the R-, L-, X-, and N-movements required in imaging and patient positioning by some conventional systems.

FIG. 2C illustrates a positioning of the patient 201 during Cephalometric imaging. In the Cephalometric imaging position, where the rotating part 220 is over the patient support means 268, 269 located at the Cephalometric head 262, the patient 201 is supported to the patient support means 268, 269.

If the upper shelf 250 as well as the rotating part 220 are in a different position than the Cephalometric imaging position, for example, in a Panoramic/CT imaging position or in an intermediate position between the Panoramic/CT and Cephalometric imaging positions—the upper shelf 250 is moved from that position to the Cephalometric imaging position by the P-movement, and then the rotating part 220 is further adjusted by the R- and L-movements so that the rotating part 220 is ready for the Cephalometric imaging.

The positioned X-ray source 265 is configured to scan the supported patient 201 by means of the X-ray beam limiting device 267 attached to the X-ray source 265 and by means of the S-movement. The detector 226—and the rotating part 220—is configured to move synchronously with the X-ray source 265 by the R-, L-, and P-movements during the Cephalometric imaging.

The X-ray beam from the X-ray source 265 is arranged to scan the patient's 201 head by rotating the X-ray source 265 and the X-ray beam limiting device 267 with the S-movement around the axis 264. Alternatively, the S-movement can be performed by moving (for example, linearly) the X-ray beam limiting device 267. It is also possible that the S-movement is provided as a vertical scanning movement instead of the horizontal S-movement, if the detector of the detector 226 used in Cephalometric imaging is positioned horizontally. Alternatively, Cephalometric imaging can be performed without the S-movement if a sufficiently large detector (so-called, "one shot" detector) is used for the one-shot Cephalometric image.

The X-ray beam is then further collimated by the Cephalometric collimator 266 and finally captured by the synchronously moved Cephalometric or combination detector in the detector 226. The system 200 simplifies the movements during the Cephalometric imaging, because no additional movement means are needed for the Cephalometric collimator 266 and the detector of the detector 226.

FIG. 2D illustrates a calibration of a Cephalometric patient support 262. In one example, the Cephalometric patient support 262 is positioned so that the laser beam LB from the laser 263 impinges on the ear buds 268. As shown in FIG. 2D laser beam LB is generated from the laser 263 (not shown in FIG. 2D), which as noted may be located in the housing H along with the X-ray source 224. The laser beam LB is projected on the surface of the X-ray imaging detector 226. In some embodiments, the X-ray imaging detector 226 has alignment markings (for example, a solid dot or an "X") on the surface facing the X-ray source 224. The alignment markings can be approximately between 120 mm and 130 mm from the bottom edge of the X-ray imaging detector 226. The laser beam LB is targeted to hit the alignment markings on the X-ray imaging detector 226. This provides a mechanism for aligning the Cephalometric patient support 262 with the alignment markings on the X-ray imaging detector 226. The plane of the alignment marking corresponds to the Frankfurt plane of the patient. Thus, it is possible to align the ear buds 268A with the Frankfurt plane of the patient. In one example, the alignment is performed manually, with an operator adjusting the first arm 260, for example, by pivoting the first arm 260, which in turn may cause Cephalometric patient support 262 to raise or lower depending on the direction of the pivot. In addition, the position of the first arm 260 with respect to the column 240 may be adjusted. For example, if the Cephalometric patient support 262 is added to the system 200 as an accessory, the height of the first arm 260 may be adjusted with respect to the column 240 by tightening bolts or screws at particular positions within mounting slots. In other embodiments, the first arm 260 may be mounted to the column using an adjustable mechanism, for example, a slidable clamp or bearing-mounted clamp, that allows vertical movement of the first arm 260 with respect to the column 240. For example, a slidable clamp with a brake may be driven by an electric motor to permit adjustment of the first arm 260 with respect to the column 240 and may be included as one of the movement devices 275. In another example, a camera (for example, part of the positioning means 227) captures an image of the laser beam projected on the X-ray imaging detector 226 and analyzes the image to determine whether the ear buds 268 are aligned with the laser beam (for example, using image analysis software stored in the memory 280). The controller 270 then controls the movement devices 275 to adjust the first arm 260 to align the ear buds 268A with the laser beam. As a consequence, the ear buds 268A are aligned with the Frankfurt plane of the patient. For example, the first arm 260 (and, in some cases, the second arm 260) may be pivoted with respect to the column 240. In other cases, an adjustable mechanism may be controlled to adjust the vertical position of the first arm 260 with respect to the column 240.

FIG. 2E is a side view of a patient illustrating a Frankfurt plane of the patient 201. The patient 201 is positioned using the adjustable ear rod 268 and the adjustable nose support 269.

In other embodiments of the system 200 where there is a single patient support, for example, the second patient support 242, techniques used to align Cephalometric patient support 262 may be applied. For example, a relationship between the laser beam LB and the chin support CS (for example, a predetermined height difference between the two) may be used to align the position of the second patient support 242 with respect to the column 240 using one or more of the adjustment mechanisms described above.

FIG. 2F illustrates the functional elements of the system 200. The system 200 includes a controller 270 that receives input from a control panel and that is configured to control the system 200, and its above-described movements and imaging processes. The controller 270 is attached, for example, to the column 240. The controller 270 includes at least one processor (portion) 272 for performing user and/or software initiated instructions and for processing data, and at least one memory (portion) 280 for storing and maintaining data, for example, instructions, software, and data files.

In addition, the controller 270 includes a data transfer portion 274 for sending control commands to, for example, the pivot, linear, height, rotating, detector, X-ray beam limiting, and collimator motors, drivers, or other means (motors, devices) 275 configured to provide the movements of the parts of the system 200, and/or receiving data from measuring devices or other detection devices 276 configured to detect the function of parts of the system 200.

In addition, the data transfer portion 274 is also configured to send control commands to the at least one of followings: at least one of X-ray source 224 and/or X-ray source 265, the detector 226, positioning means 277 (for example, at least one laser, camera, or other indication means) configured to facilitate a positioning of the patient 201 in the Panoramic imaging position and/or CT imaging position by indicating a correct positioning of the patient 201. The data transfer portion 274 is also configured to receive information from at least one of the following: the at least one X-ray source 224, 265, the detector 226, and the positioning means 277.

In addition, the controller 270 includes a user interface portion 278 which may include at least one of the following: at least one function key, a touchscreen, and a wired or wireless remote controller, for inputting control commands, and for receiving information and/or instructions.

The at least one memory 280 stores at least a data transfer application 284 for execution by the processor 272 controlling the data transfer portion 274, a user interface application 288 for execution by the processor 272 for controlling the user interface portion, and a computer program (code) 289 for controlling the function of the system 200, for example, at least the movement devices 275, detection devices 276, the at least one X-ray source 224, 265, the detector 226, and positioning means 277. In addition, execution of the computer program 289 can control, for example, imaging parameters, imaging sizes, and imaging modes.

The at least one memory 280 and the computer program 289 are configured to with the at least one processor 272, cause the system 200 at least to provide actions described in context of FIGS. 2A-2D, for example, to control positions of the detector 226 and the Cephalometric collimator 266 by at least one or two of the R-, L-, and P-movements.

The computer program 289 can be a computer program product that includes a tangible, non-volatile (non-statutory) computer-readable medium bearing a computer program 289 embodied therein for use with a computer (controller 270).

FIG. 2G illustrates one detector 226 that includes at least one detector 227a, 227b, which can provide a Panoramic, CT, and Cephalometric image.

The rotating part 220 includes moving means 230, which move the at least one 20 detector 227a, 227b relative to the rotating part 220 for positioning the at least one detector 227a, 227b for the imaging, and the detector motor 235 configured to drive the moving means 230. The detector 227a can be, for example, a Panoramic detector, which is configured to provide the Panoramic image, or a Cephalometric detector, which is configured to 25 provide a Cephalometric image and a Panoramic image. The CT detector 227b is configured to provide a CT image.

The moving means 230 can comprise, for example, at least one of rails 231a, 231b, a threaded rod 232, a conveyor unit 233, a guide unit 234 that is connected to the conveyor unit 233 and attaches the detector 227a to the rotating part 220, and a 30 guide groove 236.

The detector motor 235 moves the detector 227a by means of the threaded rod 232, which moves the conveyor unit 233 along the rails 231a, 231b so that the guide unit 234 guides the detector 227a sideways along the guide groove 236 that can be, for example, a direct, curved, or devious groove.

FIG. 2G illustrates one example of a Panoramic imaging position, wherein the X-ray source 224 and the Panoramic or Cephalometric detector 227a, which is attached to the rotating part 220, can provide the Panoramic image.

The detector 227a and the CT detector 227b are arranged successively in the Panoramic imaging position so that the detector 227a is between the X-ray source 224, 265 and the CT detector 227b—the detector 227a is in front of the CT detector 227b relative to the used X-ray source 224, 265.

In some embodiments, the CT imaging position can also be a Cephalometric imaging position, wherein the X-ray source 265 can provide together with the Cephalometric detector 227a, which is attached to the rotating part 220, the Cephalometric image. It is possible that the detector 227a is in another position relative to the CT detector 227b in Cephalometric imaging, for example, in the position according to FIG. 2G or in a position, wherein the detector 227a is displaced so that it is substantially behind the CT detector 227b. In addition, it is possible that the Cephalometric imaging can be provided when the detectors 227a, 227b are arranged successively, whereupon the Panoramic imaging position is also the Cephalometric imaging position. In some embodiments, the first X-ray source 224 and the combination detector 227, which is attached to the rotating part 220, are used for providing the Panoramic image and the CT 30 image. The second X-ray source 265 and the combination detector 227, which is attached to the rotating part 220, are used for providing the Cephalometric image. The combination detector 227 can be driven similarly as the detector 227a in the detector 226 illustrated in FIG. 2G by for example, similar moving means 230, but not necessary by all its movements.

The Panoramic image is taken when the combination detector 227 has been driven to the Panoramic imaging position similarly as illustrated in FIG. 2G, whereupon the combination detector 227 is in a front position.

The CT and Cephalometric images are taken when the combination detector 227 has been driven to the CT/Cephalometric imaging position whereupon the combination detector 227 is in a back position. In addition, the combination detector 227 can be positioned by means of the moving means 230 and by means of at least one of the R-, L-, and P-movements. Alternatively, the combination detector 227 can be positioned by means of at least one of the R-, L-, and P-movements.

So, the combination detector 227 can be moved between at least of two of the Panoramic, CT, and Cephalometric imaging positions by means of the moving means 230 and/or by means of at least one of the R-, L-, and P-movements.

Figure 3:
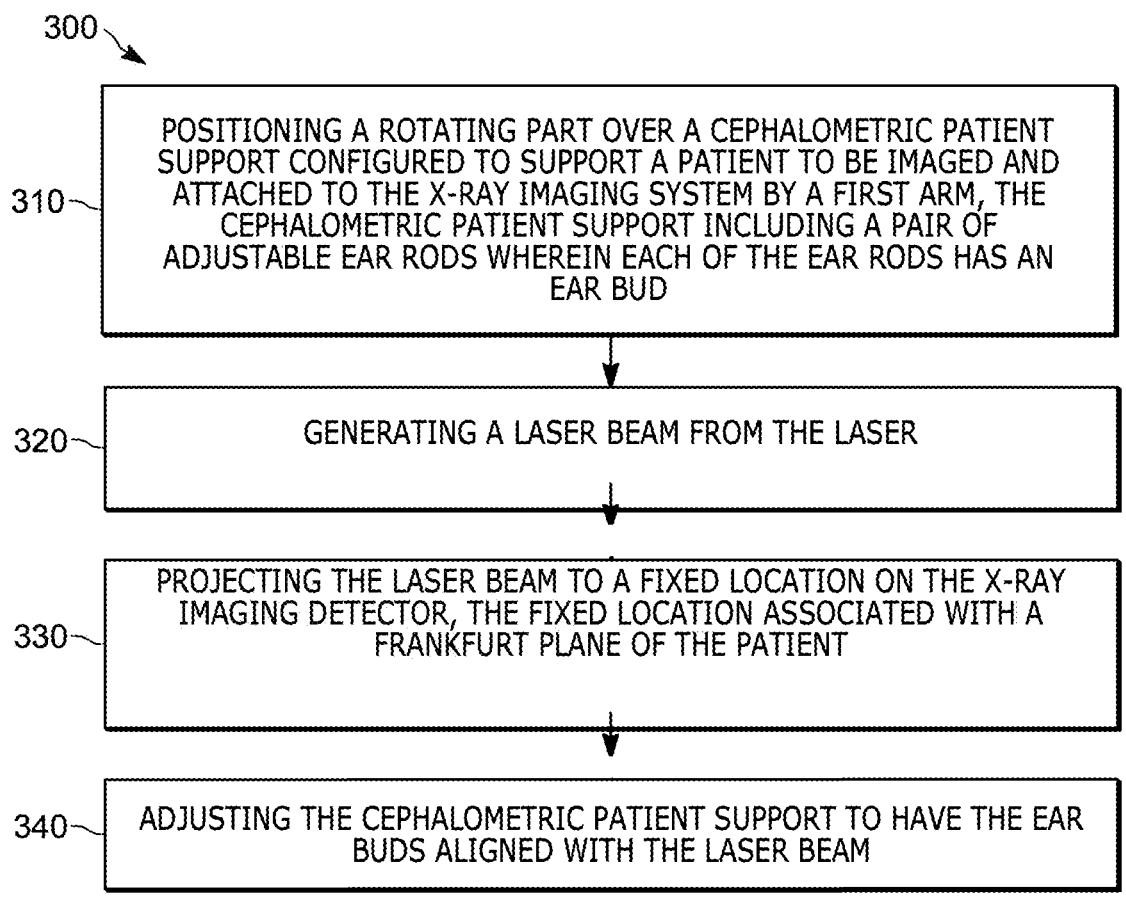
FIG. 3 is a flow chart of method for calibrating an X-ray imaging system in accordance with some embodiments.

FIG. 3 is a flow chart of method 300 calibrating an X-ray imaging system in accordance with some embodiments. The method 300 includes positioning the rotating part 220 over the Cephalometric patient support 262 attached to the column 240 via the first arm 260 (at block 310). As noted, the Cephalometric patient support 262 includes the pair of adjustable ear rods 268 and the adjustable nose support 269. Each of the ear rods 268 has an ear bud 268A. The method 300 also includes generating laser beam LB from the laser 263 (at block 320).

The method 300 further includes projecting the laser beam to a fixed location on the X-ray imaging detector 226, the fixed location associated with a Frankfurt plane of the patient (at block 330). The method 300 also includes adjusting the Cephalometric patient support 262 by aligning the ear buds 268A with the laser beam (at block 370).

Some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

Embodiments and examples have been explained above with reference to the aforesaid embodiments and the several advantages have been demonstrated. It is clear that the invention is not restricted to these embodiments, but includes other embodiments and the following claims.

What is claimed is:

1. An X-ray imaging system for medical imaging, the X-ray imaging system comprising:
   a column;
   an upper shelf coupled to the column;
   a rotating part rotatably coupled to the upper shelf and having a rotation axis with respect to the upper shelf, the rotating part including a first X-ray source, a laser, and an X-ray imaging detector, the first X-ray source and the X-ray imaging detector configured to provide an image by means of at least a rotational movement (R) of the rotating part;
   a Cephalometric patient support configured to support a patient to be imaged, attached to the column by a first arm, and including a pair of adjustable ear rods, wherein each of the ear rods has an ear bud;
   wherein the laser is configured to generate and project a laser beam to a fixed location on the X-ray imaging detector, the fixed location associated with a Frankfurt plane of the patient; and
   wherein the Cephalometric patient support is adjustable to align the ear buds with the laser beam.

2. The X-ray imaging system of claim 1 further comprising:
   a second X-ray source attached to the column by a second arm and includes an X-ray beam limiting device, wherein the second X-ray source is positioned to generate an X-ray beam and in combination with the X-ray imaging detector provide a Cephalometric image; and
   a controller configured to control a scanning movement (S) and a height movement ($Z_c$) of the second X-ray source.

3. The X-ray imaging system of claim 2, wherein the rotating part comprises a Cephalometric collimator configured to collimate an X-ray beam from the second X-ray source during Cephalometric imaging and the rotating part is configured to be positioned over the Cephalometric patient support by the pivot movement (P).

4. The X-ray imaging system of claim 2, wherein the rotation axis of the second X-ray source passes through a focal spot of the second X-ray source.

5. The X-ray imaging system of claim 2, wherein the second X-ray source is configured to scan the patient by means of the X-ray beam limiting device attached to the second X-ray source and the scanning movement (S), and the X-ray imaging detector is configured to move synchronously with the second X-ray source by rotational, linear, and pivot movements during Cephalometric imaging.

6. The X-ray imaging system of claim 1, further comprising a controller configured to align the laser beam generated at the first X-ray source with the fixed location on the X-ray imaging detector.

7. The X-ray imaging system of claim 1, wherein the first X-ray source and the X-ray imaging detector are configured to provide a computed tomography image when the X-ray imaging detector is attached to the rotating part, and the rotating part is configured to be positioned by at least one of rotational, linear, and pivot movements during a computed tomography imaging.

8. The X-ray imaging system of claim 1, wherein the Cephalometric patient support is adjustable to align the Cephalometric patient support with the X-ray imaging system by aligning the each buds with the laser beam while the laser beam is projected to the fixed location on the X-ray imaging detector.

9. An X-ray imaging system for medical imaging, the X-ray imaging system comprising:
   a column;
   a first X-ray source, a laser, and an X-ray imaging detector;
   a patient support configured to support a patient to be imaged and attached to the column by a first arm, and including a patient contact; and
   wherein the laser is configured to generate and project a laser beam to a fixed location on the X-ray imaging detector, the fixed location associated with a Frankfurt plane of the patient; and
   wherein the patient support is adjustable to align the patient contact with the laser beam.

10. The X-ray imaging system of claim 9 further comprising:
    a second X-ray source attached to the X-ray imaging system by a second arm;
    a controller configured to control a scanning movement (S) and height movement ($Z_c$) of the second X-ray source.

11. The X-ray imaging system of claim 10, further comprising an upper shelf and a rotating part attached to the upper shelf, wherein the rotating part includes the first X-ray source, the laser, the X-ray imaging detector, and a Cephalometric collimator configured to collimate an X-ray beam from the second X-ray source during Cephalometric imaging and the rotating part is configured to be positioned over the Cephalometric patient support by a pivot movement.

12. The X-ray imaging system of claim 10, wherein a rotation axis of the second X-ray source passes through a focal spot of the second X-ray source.

13. The X-ray imaging system of claim 10, wherein the second X-ray source is configured to scan the patient by means of an X-ray beam limiting device attached to the second X-ray source and a scanning movement, and the X-ray imaging detector is configured to move synchronously with the second X-ray source by rotational, linear, and pivot movements during Cephalometric imaging.

14. The X-ray imaging system of claim 9, wherein a controller is configured to align the laser beam generated at the first X-ray source with the fixed location on the X-ray imaging detector.

15. The X-ray imaging system of claim 9, wherein the first X-ray source and the X-ray imaging detector are configured to provide a computed tomography image when the X-ray imaging detector is attached to the rotating part, and the rotating part is configured to be positioned by at least one of rotational, linear, and pivot movements during a computed tomography imaging.

16. The X-Ray imaging system of claim 9, wherein the patient support is adjustable to align the patient support with the X-ray imaging system by aligning the patient contact with the laser beam while the laser beam is projected to the fixed location on the X-ray imaging detector.

17. A method for calibrating an X-ray imaging system including a column, an upper shelf coupled to the column, a rotating part rotatably coupled to the upper shelf and having a rotation axis with respect to the upper shelf, the rotating part comprising an X-ray source, a laser, and an X-ray imaging detector, the method comprising:
positioning the rotating part over a patient support attached to the column with a first arm, the patient support including a patient contact;
generating a laser beam from the laser;
projecting the laser beam to a fixed location on the X-ray imaging detector, the fixed location associated with a Frankfurt plane of the patient; and
adjusting the patient support to align the patient contact with the laser beam while the laser beam is projected to the fixed location on the X-ray imaging device.

18. The method of claim 17, further comprising aligning the patient support with the X-ray imaging system by adjusting the patient support to align the patient contact with the laser beam while the laser beam is projected to the fixed location on the X-ray imaging device.

* * * * *